(12) United States Patent
Martius (10) Patent No.: US 11,089,978 B2
(45) Date of Patent: Aug. 17, 2021

(54) DETECTION APPARATUS AND METHOD FOR DETECTING A RESPIRATORY MOVEMENT, COMPUTER PROGRAM, COMPUTERREADABLE STORAGE MEDIUM, AND MEDICAL DEVICE

(71) Applicant: Siemens Healthcare GmbH, Erlangen (DE)

(72) Inventor: Sebastian Martius, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/715,934

(22) Filed: Dec. 16, 2019

(65) Prior Publication Data

US 2020/0187889 A1   Jun. 18, 2020

(30) Foreign Application Priority Data

Dec. 17, 2018  (DE) .......................... 102018221960.5

(51) Int. Cl.
*A61B 5/113* (2006.01)
*A61B 5/00* (2006.01)
(Continued)

(52) U.S. Cl.
CPC .............. *A61B 5/113* (2013.01); *A61B 5/277* (2021.01); *A61B 5/6891* (2013.01);
(Continued)

(58) Field of Classification Search
CPC ............ A61B 5/05; A61B 6/527; A61B 5/113
See application file for complete search history.

(56) References Cited

U.S. PATENT DOCUMENTS 3,150,375 A   9/1964 Bevan
4,289,142 A   9/1981 Kearns
(Continued)

FOREIGN PATENT DOCUMENTS

CN        102683837 B    4/2014
DE    102009021232 B4   11/2010
(Continued)

OTHER PUBLICATIONS

Sundara-Rajan et al. "Fringing Electric and Magnetic Field Sensors." Encyclopedia of Sensors. 2006. (Year: 2006).*
(Continued)

*Primary Examiner* — Meredith Weare
(74) *Attorney, Agent, or Firm* — Lempia Summerfield Katz LLC (57) ABSTRACT

A detection apparatus and a method are provided for detecting a respiratory movement of a patient. The detection apparatus includes at least two metallic U-shaped signal coupling elements that are interleaved so that between the signal coupling elements arises at least one coupling point at which a signal may be transferred between the two signal coupling elements. Analysis electronics are configured to detect a change in a received signal produced in a second of the signal coupling elements that is acting as a receiver in the near-field region of the first signal coupling elements as a result of a signal given for one of the signal coupling elements that is acting as a transmitter being coupled into the second of the signal coupling elements, which change indicates the respiratory movement.

15 Claims, 2 Drawing Sheets

(51) Int. Cl.
    *A61B 6/00*     (2006.01)
    *A61B 5/277*     (2021.01)
    *H04B 5/00*     (2006.01)

(52) U.S. Cl.
    CPC ............ *A61B 5/7285* (2013.01); *A61B 6/527* (2013.01); *H04B 5/0012* (2013.01)

(56) References Cited

U.S. PATENT DOCUMENTS

| | | | |
|---|---|---|---|
| 9,933,469 B1 | 4/2018 | Ridenour | |
| 2008/0208063 A1* | 8/2008 | Brauers | A61B 5/04085 600/481 |
| 2009/0284440 A1 | 11/2009 | Weidmann et al. | |
| 2010/0292559 A1 | 11/2010 | Hahnemann | |
| 2013/0165770 A1 | 6/2013 | Li | |
| 2014/0276090 A1* | 9/2014 | Breed | A61B 5/14546 600/473 |
| 2015/0002331 A1 | 1/2015 | Allmendinger | |
| 2017/0055910 A1 | 3/2017 | Kim et al. | |
| 2019/0289840 A1* | 9/2019 | Kaye | A01M 23/00 |

FOREIGN PATENT DOCUMENTS

| | | |
|---|---|---|
| DE | 102013212819 A1 | 1/2015 |
| EP | 2117077 A1 | 11/2009 |
| EP | 2659832 A1 | 11/2013 |
| JP | S55108343 A | 8/1980 |
| JP | S5612104 A | 2/1981 |
| JP | H0346585 A | 2/1991 |
| KR | 20060019443 A | 3/2006 |

OTHER PUBLICATIONS

Areekath et al. "An Electric-Field Based Breathing Rate Monitor." 2018 IEEE International Symposium on Medical Measurements and Applications (MeMeA). Jun. 11-13, 2018. (Year: 2018).*

Sivayogan, Thuvatahan. "Design and Development of a Contactless Planar Capacitive Sensor." Master's thesis, University of Toronto, 2013. http://hdl.handle.net/1807/42936 (Year: 2013).*

Yama, Yoshihiro. "Unrestrained facile measurement of narrow-band ECG and respiratory variation in infants with a capacitive sheet-type sensor." Bio-medical Engineering 47.1 (2009): 42-50-Abstract. (Year: 2009).*

German Office Action for German Application No. 10 2018 221 960.5 dated Oct. 15, 2019.

Ghahremani, Ahmadreza, Melika Roknsharifi, and James Hamill. "Mono-static CW Doppler Radar for Quantifying Respiratory Motion during PET/CT scans." 2017 IEEE Nuclear Science Symposium and Medical Imaging Conference (NSS/MIC). IEEE, 2017.

Hahnel, Ronny, et al. "Antenna and radar front-end design for heartbeat detection for triggering purposes of medical devices." Proceedings of the 8th International Conference on Body Area Networks. ICST (Institute for Computer Sciences, Social-Informatics and Telecommunications Engineering), 2013.

Pfanner, F., et al. "Monitoring respiratory and cardiac motion in CT using a continuous wave Doppler radar." ECR-Congress, 2013. pp. 1-12.

German Office Action for German Application No. 10 2018 221 960.5 dated Oct. 15, 2019, with English Translation.

German Grant Decision for German Application No. 10 2018 221 960.5 dated Dec. 17, 2019, with English Translation.

Japanese Office Action for Japanese Application No. 2019-210453 dated Mar. 10, 2020, with English translation.

Chinese Office Action for Chinese Application No. 201911299211.9 dated Sep. 3, 2020, with English translation.

Japanese Office Action for Japanese Application No. 2019-210453 dated Sep. 1, 2020, with English translation.

Japanese Notice of Allowances for Japanese Application No. 2019-210453 dated Dec. 10, 2020, with English translation.

Chinese Office Action for related Chinese Patent Application No. 201911299211.9, dated May 20, 2021, with English translation.

* cited by examiner

DETECTION APPARATUS AND METHOD FOR DETECTING A RESPIRATORY MOVEMENT, COMPUTER PROGRAM, COMPUTERREADABLE STORAGE MEDIUM, AND MEDICAL DEVICE

CROSS REFERENCE TO RELATED APPLICATIONS

This application claims the benefit of DE 102018221960.5, filed on Dec. 17, 2018 which is hereby incorporated by reference in its entirety

FIELD

Embodiments relate to a detection apparatus and to a method for detecting a respiratory movement of a patient.

BACKGROUND

Many device-based methods in medical engineering depend on accurate position or motion information about a patient under examination or under treatment, and/or are prone to errors resulting from changes in position or movements of the patient. This may apply to imaging methods and applications, for example, just as it may to oncological beam therapy, for instance. In the latter case, tumors are exposed to a high dose of radiation in a targeted manner to stem their growth or ideally even kill them. In the therapy, the aim is for healthy tissue in an area surrounding the particular tumor to be affected as little as possible. Depending on the location of the particular tumor, respiratory movement of the patient concerned may cause the tumor to move during a treatment, for example, to move out of a beam path or focus of radiation intended to treat the tumor. This may then result in surrounding healthy tissue rather than the tumor entering the beam path or the focus and being damaged undesirably. Therefore, to avoid this, accurately targeted irradiation is needed that may only be achieved when the respiratory movement is known.

In imaging methods, the respiratory movement may cause fuzzy or blurred images, for example, that then prevent any accurate or reliable diagnosis, or spatial association or registration with other data.

For example, thoracic or respiratory belts or breathing detectors based on pressure or strain sensors may be used to detect the respiratory movement. Respiratory belts or breathing detectors may be strapped around the patient and may not be suitable for all uses or individual cases, for example because Respiratory belts or breathing detectors may enter the beam path or obstruct an interventional procedure, and also have a limited sensitivity.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide improved detection of respiratory movement of a patient.

A detection apparatus is configured to detect respiratory movement of a patient. The detection apparatus includes at least two metallic signal coupling elements that are at least substantially U-shaped. The signal coupling elements are arranged on a substrate such that the signal coupling elements are interleaved, e.g. interlocked, without touching, so that between every two side segments of a first signal coupling element of the signal coupling elements is arranged at least substantially parallel thereto a first side segment of a second signal coupling element of the signal coupling elements. A second side segment of the second signal coupling element is arranged outside a region surrounded on three sides by the first signal coupling element.

Thus, each of the signal coupling elements includes two side segments that are arranged, or run, i.e. extend, at least substantially parallel to each other, and a base segment, that in each case joins together the two side segments. The segments may differ, for example, in terms of their arrangement or orientation, but equally the segments may have, for example, different widths and/or lengths. The individual signal coupling elements may each be formed as a single piece, and therefore the individual segments do not have to exist as separate components.

In addition, the detection apparatus includes an electronic circuit connected to the signal coupling elements. The electronic circuit is configured to detect a change in a received signal. The change indicates, i.e., signifies or represents, or characterizes the respiratory movement. Coupling a signal given for one of the signal coupling elements that is acting as a transmitter into a second of the signal coupling elements produces the received signal. The second of the signal coupling elements acts as a receiver and is located in a near-field region of the first signal coupling element. At a coupling point at which the signal from the first signal coupling element is transferred or cross-coupled to the second signal coupling element, a distance between the two signal coupling elements may be less than $4\lambda$ or less than $\lambda/2\pi$, where $\lambda$ is a specified wavelength of the signal given for detecting the respiratory movement for the signal coupling element of the signal coupling elements that is currently acting as a transmitter.

The wavelength $\lambda$ may be specified, for example, by legal regulations intended to prevent interference or by frequency bands legally specified or reserved for the purpose of voice applications. For example, a size or length of the signal coupling elements is matched to the wavelength $\lambda$, where the signal coupling elements may have a length of $\lambda/2$ along the U-shaped course or the U-shaped extent, i.e. along the one side segment, then the base segment and then the second side segment.

In the arrangement of the signal coupling elements, that may be regarded as antennas, for instance, at least one coupling point arises between every two mutually adjacent side segments of different signal coupling elements, across which coupling point the signal is coupled from one of the signal coupling elements into the nearest or other of the signal coupling elements. In the region of the coupling points, at least portions of the side segments of each pair of signal coupling elements may run at least substantially parallel to each other, and therefore the coupling or cross-coupling or transfer of the signal between the two side segments, i.e. between the two signal coupling elements, may be understood in the sense of cross-talk.

A coupling or transfer behavior may depend, inter alia, on a distance between the two signal coupling elements, for example, between the two side segments forming or encompassing the particular coupling point. Since the two side segments run at least substantially parallel to each other in the region of the coupling point, a respective capacitance arises. External influences, for instance materials or objects or fields brought into a region of the coupling point, or corresponding variations or movements, may affect or change this capacitance. Influencing the capacitance in this way in turn causes a change in the coupling or transfer behavior at the coupling point concerned. Thus if the detection apparatus is arranged in the region of the patient, for instance above or below the patient, then the patient's respiratory movement will cause a change in the capacitance, or in the coupling or transfer behavior, at the respective coupling point, and hence a change in the resultant received signal, even without any change in the signal given for the signal coupling element acting as transmitter.

A corresponding calibration may be carried out, for example, to detect the respiratory movement, i.e., to distinguish a change in the received signal caused by the respiratory movement, for instance from changes produced by other effects or influences. Equally, for example, it may be stipulated as a condition that only those changes that repeatedly reverse, i.e. that repeat at least substantially or approximately rhythmically or regularly or periodically, are detected as respiratory movement or as a consequence of the respiratory movement. Since typical breathing is not regular or periodic in the strictly mathematical sense, corresponding deviations, for example, may be permitted, for example by corresponding defined intervals, threshold values, value ranges, or suchlike Thus, for example, a sub-, pseudo-, or quasi-periodic change in the received signal may be detected as respiratory movement.

The arrangement provides for a compact design of the detection apparatus. For example, the interleaved arrangement provides for a multiplicity of coupling points to be implemented with a high spatial density, for example in comparison with other antenna types such as a simple rectangular patch antenna. Thus, a plurality of signal coupling elements may be suitably interleaved, i.e. as a chain or a row which facilitates a spatial resolution in the detection of the respiratory movement. The high spatial density of coupling points that may be achieved for a given wavelength or frequency of the signal used for detection provides for fine scanning or sampling of a surface region covered by the detection apparatus, i.e. a high spatial resolution of the detected respiratory movement.

The detection apparatus may include a low-profile and space-saving design, for example compared with conventional respiratory belts placed around the patient's chest. The arrangement composed of the signal coupling elements may be integrated, for example, in a patient couch or a patient table on which the patient concerned then lies. The respiratory movement may thus be detected without any external sensors and hence without an examination or treatment of the patient being affected or obstructed. As a result of the progress made in recent years and decades in the field of electronic signal generation, signal detection and signal processing, for example, in the accuracy and also temporal and frequency resolution that may be achieved, embodiments may detect the respiratory movement with significantly improved accuracy and sensitivity, for example compared with the respiratory belts that may be based, for example, on an at least partially mechanical principle.

In an embodiment, the signal coupling elements each include a length of between 16.1 cm and 17.6 cm, for example 16.82 cm, measured along their U-shaped course or U-shaped extent. The numerical values may also include a tolerance of 5% for example. The lengths correspond to the length from one end to the opposite end of the particular signal coupling element in the longitudinal extension direction, where the signal coupling element to be unfolded into the form of a straight line instead of its U-shaped form. Since the signal coupling elements as described act, or may be regarded, as antennas, with the length equal to the half wavelength of a preferentially transmitted or received signal, the lengths of the signal coupling elements correspond to signal frequencies from approximately 930 MHz to approximately 853 MHz, for example, approximately 892 MHz which provides the signal coupling elements to be used for different suitable frequency bands, for example, both for frequencies of, or around, 915 MHz, and for frequencies of, or around, 868 MHz. The detection apparatus may be employed in a versatile manner worldwide.

In an embodiment, the signal coupling elements are each made of a metallic layer of thickness 50 μm maximum, for example, of thickness less than 25 μm. The thickness in is a material thickness of the actual metallic signal coupling elements perpendicular to respective main extension planes, and thus accordingly also perpendicular to a main extension plane or main extension direction of the substrate. The signal coupling elements may be fabricated, for example, from a layer made of aluminum, copper or a corresponding alloy or a similar metallic material, of approximate thickness 17 μm that provides not only for the detection apparatus to have a thin design and hence a configuration that may be adapted to suit given individual installation-space conditions, but may make the signal coupling elements also at least substantially transparent to X-ray radiation. The detection apparatus may be used in X-ray based medical devices without, for example, impairing a beam intensity or a resultant image quality. The substrate may be configured such that an overall thickness or overall height of an antenna system of the detection apparatus, i.e. of the substrate, of the signal coupling elements and of any additional functional layers or coatings of the substrate that may be present, equals at most 0.5 mm. The detection apparatus or antenna system may thereby be integrated easily for instance in a patient table of a medical device, and is thereby always readily available, may be operated or used consistently, and is protected from damage.

In an embodiment, the substrate is made of a plastic material and metalized on a rear face that faces away from the signal coupling elements. The signal coupling elements may thus be arranged or applied on a top face of the substrate that is opposite the rear face. This top face may then be arranged to face the patient. The metalized, i.e. metal-coated, rear face of the substrate, that may be arranged to face away from the patient, may prevent or reduce any unwanted influence on the electrical properties of the signal coupling elements, of the coupling points or of an associated surrounding three-dimensional or two-dimensional area. For example, patient tables or patient couches of medical devices are often fabricated from, or using, carbon fibers, that, without the continuous substrate metallization, preferably over the full surface of the rear face, may alter, for example, transmit and/or receive properties of the signal coupling elements and hence could impair the function of the detection apparatus. However, the rear-face metallization prevents an influence of this type, or minimizes or limits such an influence to such an extent that the function of the detection apparatus is not, or not significantly, impaired when it is arranged and operated on a corresponding patient table or integrated in the patient table close to the surface. Fabricating the substrate out of the plastic material, for instance out of glass-fiber reinforced plastic, provides low-cost fabrication of the detection apparatus using established fabrication methods and may provide electrical isolation between the signal coupling elements and the rear-face metallization.

In an embodiment, a method for detecting the respiratory movement of the patient by the detection apparatus is provided. In the method, the electronic circuit is used to place a defined, for example, continuous signal onto precisely one first signal coupling element of the signal coupling elements. The electronic circuit may include a suitable signal generator, an amplifier and/or suchlike. In addition, in the method, the electronic circuit is used to measure a received signal that, as a result of the transmitted signal being coupled out of the first signal coupling element across a coupling point into a second of the signal coupling elements that is interleaved with the first signal coupling element in its near-field region, arises or is induced in the second signal coupling element.

In another act, with the detection apparatus arranged in the region of the patient, the respiratory movement is detected as a change, for example, a repeatedly reversing change, in the received signal that occurs without a corresponding change in the transmitted signal. As a result of the respiratory movement, the received signal may, for example, repeatedly weaken in correspondence with a breathing rhythm of the patient, with increases in signal lying between each repeated weakening. Thus, a direction or sign of the change in the received signal accordingly reverses repeatedly in this case. This is caused by the coupling or transfer of the transmitted signal from the signal coupling element currently acting as transmitter into the signal coupling element currently acting as receiver at the coupling point is affected by, or dependent on, a capacitance of the coupling point or at the coupling point. The capacitance may in turn be affected by water molecules located in a surrounding area or a region of the coupling point. During the respiratory movement of the patient, tissue regions of the patient that contain water move relative to the coupling point, and therefore relative to the signal coupling elements and to the detection apparatus that leads to a change in the capacitance and hence in the coupling or transfer characteristic at the coupling point, and hence to an electronically detectable change in the received signal. The change in the received signal may not be correlated with a change in the transmitted signal. For example, the transmitted signal may be constant or may change or be modulated in a defined manner. Such a temporal change or modulation in the transmitted signal would, however, for example, without any further external influences, always correspond or be correlated directly, and in a predictable manner, to an associated temporal change or modulation in the received signal, and therefore does not negatively affect any additional change in the received signal caused by the respiratory movement or the detection thereof.

The electronic circuit may be configured to determine, by analyzing the change in the received signal, a respiratory phase, i.e. a phase or a segment of the respiratory movement or of a respiratory cycle, that prevails at that time. Examples of such respiratory phases that may be determined or detected automatically are inspiration and expiration. For example, depending on the sensitivity of the detection apparatus used and/or, for instance, depending on the placement of the patient relative to the detection apparatus, further respiratory phases may additionally be determined or detected automatically, for instance phases such as a start or first sub-segment of an end or last sub-segment of the inspiration and/or expiration respectively, and/or, for example, a center time of the particular respiratory cycle, and/or, for example, a reversal point, at which a direction of movement of at least one sub-region of the patient relative to the detection apparatus reverses, for instance between inspiration and expiration.

A corresponding medical device, for example, may be controlled according to the respiratory movement or respiratory phase detected. If the medical device is an irradiation device, for example, then the irradiation may be pulsed and synchronized automatically with the detected respiratory movement or respiratory phase, so that the radiation happens always in the same respiratory phase or at the same point in the respiratory cycle, i.e. each time preferably for an identical situation or position of the patient. It is hence possible to target tumor tissue, for example, reliably and accurately. Accordingly, a medical imaging device, for example, may be controlled automatically on the basis of the respiratory movement or respiratory phase detected synchronously therewith, so that it acquires a single image in the same respiratory phase or at the same point in time within each respiratory cycle which reduces motion blurring, and makes it easier to overlay or register the individual images with one another, and thus ultimately improves image quality.

In another embodiment, a detection apparatus includes more than two signal coupling elements. The two side segments of at least one of the signal coupling elements laterally enclose precisely one side segment each of two other signal coupling elements of the signal coupling elements. Thus, the plurality of signal coupling elements are interleaved or interlinked without touching in a longitudinal direction or in a meandering pattern. For example, eight signal coupling elements may be arranged in a longitudinal direction, that may extend, for example, at least substantially perpendicular to a longitudinal extent of the side segments of the signal coupling elements.

By arranging the plurality of signal coupling elements in a row in this way, a correspondingly larger surface area may be covered in which respiratory movements may be detected by the detection apparatus. In addition, a plurality of such rows of signal coupling elements interleaved in the longitudinal direction may be provided to be able to cover a correspondingly larger surface area in the transverse direction, i.e. at right angles to the longitudinal direction, and achieve a corresponding spatial resolution in the detection of the respiratory movement.

In an embodiment, one of the signal coupling elements that is acting as a transmitter may be interchanged on the basis of a defined scheme according to a specified rhythm. At a first point in time, a first of the signal coupling elements may thus act as a transmitter. Once a signal transmitted or transferred by this signal coupling element has been measured as a corresponding received signal, then at a later, second point in time, another of the signal coupling elements may then act or be switched as a transmitter. For example, in one such step including transmitting and receiving or measuring, that signal coupling element of the signal coupling elements that acted as a receiver in a preceding step, may be used as a transmitter. This may be continued until a signal coupling element of the signal coupling elements that is acting as a receiver in the current step forms one end of the arrangement of signal coupling elements. Then the arrangement composed of signal coupling elements may be cycled through again, for instance in the reverse direction or according to a defined pattern, by suitable interchange of the signal coupling element currently acting as a transmitter. A three-dimensional or two-dimensional area may be scanned or sampled while detecting the respiratory movement with a spatial resolution. In addition, the procedure may make the detection of the respiratory movement less susceptible to a placement of the patient relative to the detection apparatus, and, if applicable, make it possible to determine or identify the respiratory phase more accurately or more reliably, because different regions of the patient may move differently during the respiratory movement, for example, within a respiratory cycle or in different respiratory phases. Thus, the respiratory movement may be detected accurately and with spatial resolution, for instance given an asymmetry of the patient, given an asymmetric respiratory movement and/or given an imprecise or unknown placement or orientation of the patient relative to the signal coupling elements.

In an embodiment, a computer program or computer program product is provided that includes commands or control instructions that on execution of the computer program by a data processing facility, for example of a medical device, cause this facility to perform automatically or semi-automatically.

In an embodiment, a computer-readable storage medium, on that is stored at least one embodiment of the computer program or computer program product is provided.

In an embodiment, a medical device, that includes at least one embodiment of the detection apparatus is provided. The medical device may be an irradiation device or an imaging device, for example. The medical device may be configured to execute or perform the method. The medical imaging device may include, for example as part of the electronic circuit, a computer-readable storage medium and a processor, for instance a microprocessor, microchip or microcontroller, connected thereto for executing the computer program stored on the storage medium. The medical device may be the medical device mentioned in association with the method. The medical device may include individual, several or all of the attributes and/or components mentioned in association with the method.

In an embodiment, the medical device includes a patient table or a patient couch having a reclining surface for the patient. The signal coupling elements of the detection apparatus are integrated in the patient table, for example in the reclining surface. To prevent the signal coupling elements being damaged, they may be covered, for example, by an electrically non-conductive, for example electrically permeable, protective layer, that may then from a surface of the patient table, for example, of the reclining surface. Hence the signal coupling elements may then be arranged close to the surface and may thereby detect the respiratory movement accurately and reliably while not coming into direct contact with the patient, whereby it is possible to avoid not only any damage, as described, but also the signal coupling elements being short-circuited, for example.

DETAILED DESCRIPTION

Figure 1:
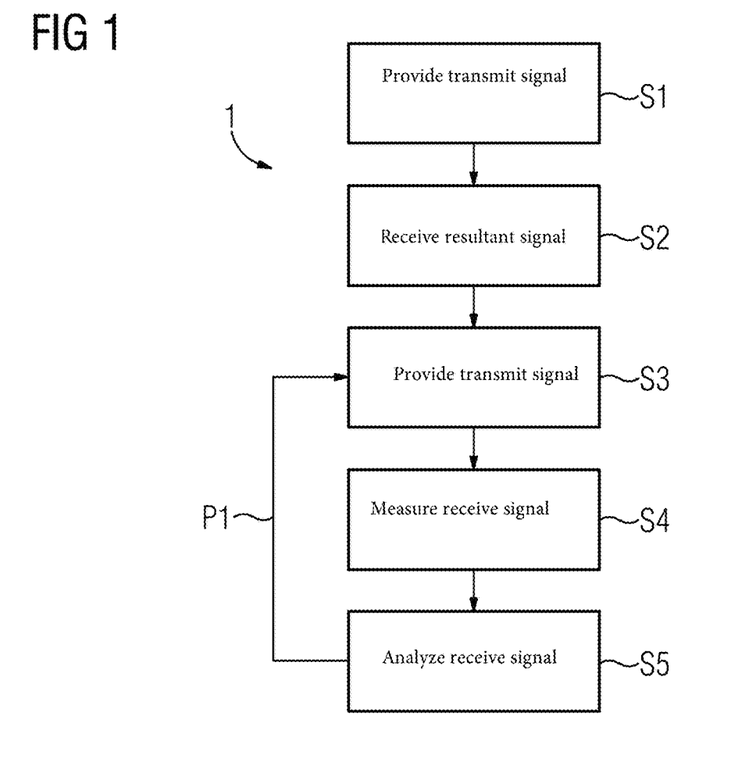
FIG. 1 depicts a schematic flow diagram as an example of a method for detecting a respiratory movement of a patient according to an embodiment.
Figure 2:
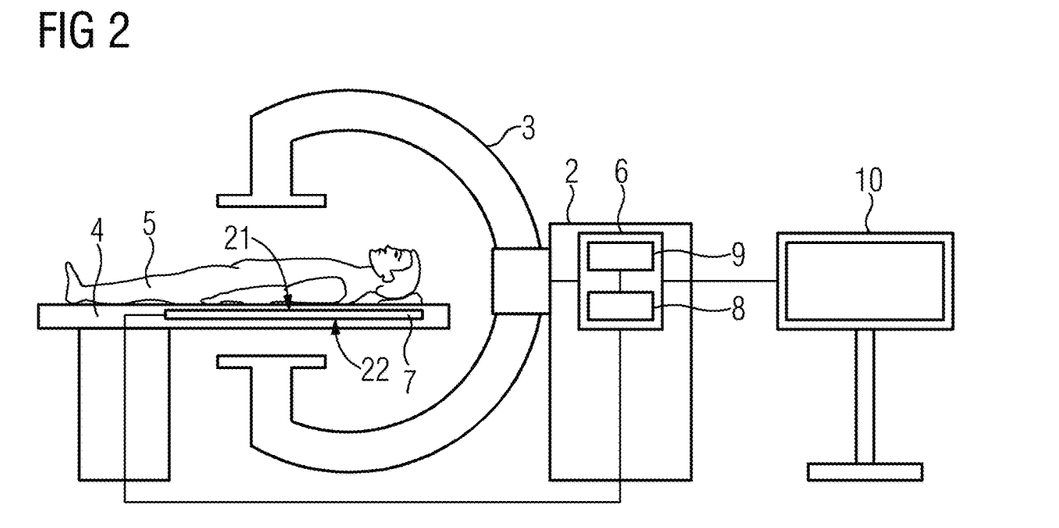
FIG. 2 depicts a schematic diagram of a medical device including a detection apparatus for detecting a respiratory movement of a patient according to an embodiment.

FIG. 1 depicts a schematic flow diagram 1 as an example of a method for detecting a respiratory movement of a patient 5 (see FIG. 2). The method may be performed, for example, by a medical device 2 shown schematically in FIG. 2. The medical device 2 includes a movable mount 3, for example a C-arm, on which may be arranged, for example, a radiation source for irradiation purposes or for imaging. In addition, the medical device 2 includes a patient table 4, on which the patient 5 is placed in a region of influence of the medical device 2, of its radiation source, for example.

The medical device 2 also includes a data processing facility 6, that is coupled to an antenna array 7 integrated in the patient table 4. The data processing facility 6 and the antenna array 7 together form a detection apparatus for detecting the respiratory movement of the patient 5. The data processing facility 6 may include, for example, a signal generating component, i.e., a signal generator, and electronic circuit, to place electrical signals onto the antenna array 7, and to measure and analyze signals measured or received by the antenna array 7.

To perform the method illustrated schematically in FIG. 1, the data processing facility 6 includes a computer-readable storage medium 8 and a processor 9 connected thereto. Stored on the storage medium 8 is a computer program, that translates into code the method steps of the method according to the flow diagram 1, i.e. executes the method, when executed by the processor 9. The method steps of the method, i.e. of the flow diagram 1, may therefore be, or may represent, program modules or function modules or code blocks of the computer program.

In addition, a display 10 is provided that is connected to the data processing facility 6. The display 10 may be used, for example, to output or visualize the detected respiratory movement or respiratory phase, for instance in the form of a respiratory curve and/or as a suitable indication of the respiratory phase. The data processing facility 6 may also be connected to additional component of the medical device 2, and be used, i.e. configured, for example, as a controller for the components, for instance the radiation source mentioned.

Figure 3:
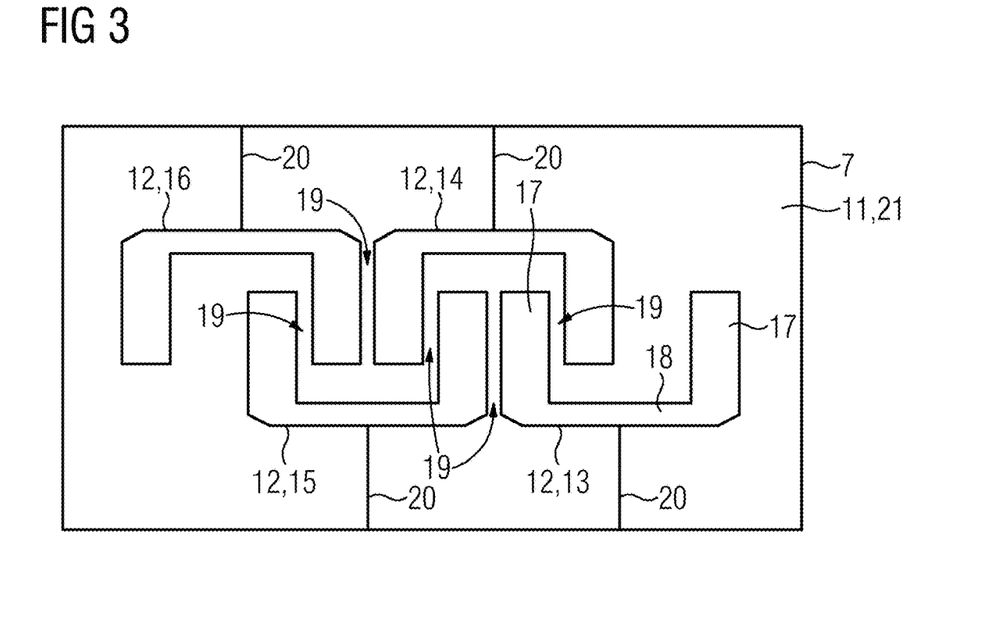
FIG. 3 depicts a schematic plan view of an antenna system of a detection apparatus for detecting a respiratory movement according to an embodiment.

There exist different frequency bands in which the detection apparatus is able, or is allowed, to work, i.e. to be operated, in compliance with regulations. The detection apparatus or the antenna array 7 may cover as many of the corresponding frequency bands as possible. Furthermore, for positioning that is as easy and versatile as possible, the antenna array 7 may include an installation height that is as low as possible, for instance not exceeding 0.5 mm. In addition, the antenna array 7 may be transparent as possible to X-rays while being as compact as possible.

To detect the respiratory movement of the patient 5 while satisfying the stated requirements, the antenna array 7, as shown schematically in FIG. 3, includes an interleaved arrangement of a plurality of metallic signal coupling elements 12 arranged on a substrate 11 made of a plastic material, for example, a first signal coupling element 13, a second signal coupling element 14, a third signal coupling element 15, and a fourth signal coupling element 16. The signal coupling elements 12 each include two side segments 17 arranged at least substantially parallel to each other, and a base segment 18, that joins together the two respective side segments 17. The side segments 17 and base segment 18 are labeled solely on the first signal coupling element 13 for the sake of clarity.

By virtue of the interleaved arrangement of the signal coupling elements 12, every two side segments 17 from different signal coupling elements of the signal coupling elements 12 extend in portions at least substantially parallel to each other at a plurality of coupling points 19. Via the coupling points 19, a transmitted signal may be transferred from a signal coupling element of the signal coupling elements 12 that is acting as a transmitter to a signal coupling element of the signal coupling elements 12 that is adjacent at that particular coupling point 19 and then accordingly acting as a receiver. If, for example, the transmitted signal is given for the first signal coupling element 13, then by the transmitted signal being coupled into the second signal coupling element 14, for instance, a corresponding received signal may be picked up at this signal coupling element. Additionally, or alternatively, the received signal may be picked up at the third signal coupling element 15, for example.

To place the transmitted signal onto the signal coupling element of the signal coupling elements 12 that is currently being used as a transmitter, and to measure or pick up the corresponding received signal, the signal coupling elements 12 are electrically connected to the data processing facility 6 by respective connecting lines 20.

For the array depicted in FIG. 3 composed of the four signal coupling elements 12, the respective side segments 17 at each of the coupling points 19 may be spaced apart from each other by approximately 7 mm, for instance, whereas the individual coupling points 19 may be spaced apart from each other by 30 mm, for example. The embodiment of the antenna array 7 provides a compact arrangement and a high spatial density of the coupling points 19, for instance in comparison with an array composed of dual patch antennas suitable for the same frequency, for which antennas a distance between corresponding coupling points may equal 100 mm for instance. Thus, using the present arrangement or antenna shape of the antenna array 7, or of the signal coupling elements 12, more densely arranged coupling points 19 are provided than using other antenna types. Finer scanning of the patient 5 lying above the antenna array 7 may be possible.

It is the function of the antenna array 7 here to emit power towards the patient 5, and/or or receive power from there, as efficiently as possible. As the patient table 4 in which the antenna array 7 is integrated may be made of carbon, i.e. carbon fibers, for example, the patient table 4 might undesirably influence electrical properties, i.e. a transmit and/or receive property or characteristic of the antenna array 7, for example, of the signal coupling elements 12. To avoid or minimize the problems, the signal coupling elements 12 may be arranged on a top face 21 of the substrate 11 that faces the patient 5, with continuous metallization provided on a rear face 22 of the substrate 11 that is opposite the top face 21. The metalized rear face 22 is used as an electrical or electromagnetic shield for the signal coupling elements 12 against influences at the coupling points 19 on a signal transfer characteristic that are not caused by the respiratory movement of the patient 5.

Figure 4:
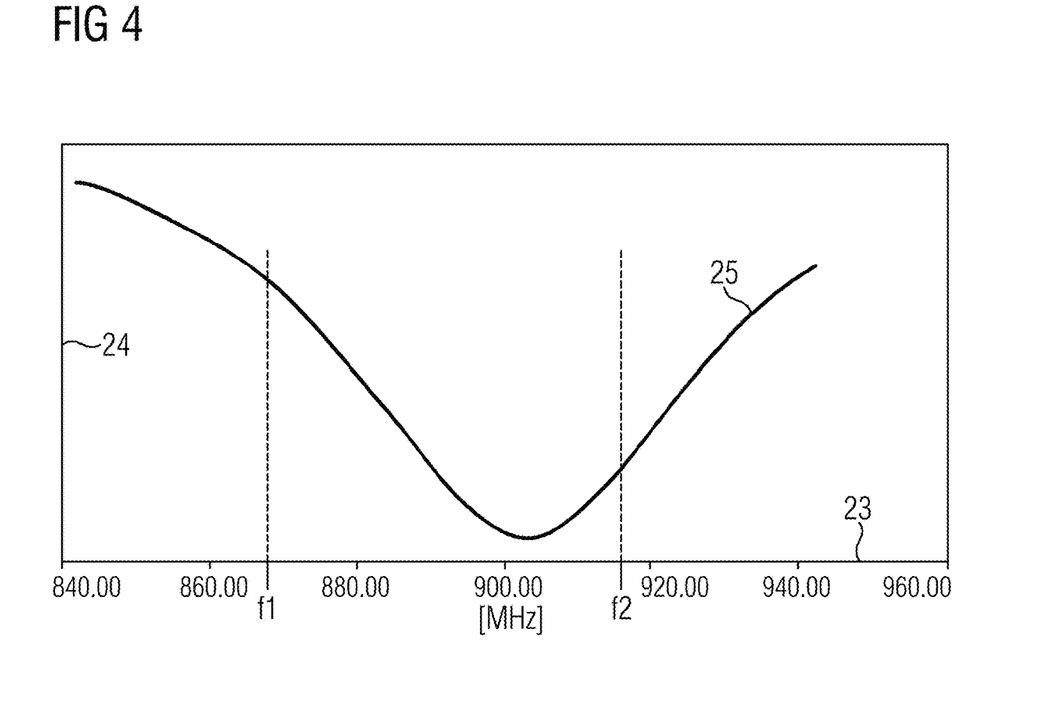
FIG. 4 depicts an attenuation curve for illustrating an electrical behavior of the antenna system of FIG. 3 at different frequencies according to an embodiment.

The individual signal coupling elements 12 may include a length of between 16 and 18 cm, for example, a length of 16.82 cm, measured along a U-shaped course in each case. The signal coupling elements are thus suitable both for signals at or around 915 MHz and for signals at or around 868 MHz and may be employed in a versatile manner worldwide. FIG. 4 depicts schematically a diagram relating to this, in which a frequency is plotted on an x-axis 23, and an attenuation is plotted on a y-axis 24. An attenuation curve 25 depicted in this diagram for the antenna array 7 or a corresponding specific implementation of such an arrangement of the signal coupling elements 12 depicts a clear minimum, in the range between 900 MHz and 908 MHz by way of example. Such an antenna array 7 is nonetheless still suitable for detecting the respiratory movement of the patient 5 and operable at the two frequencies that are standard internationally, here denoted by f1=868 MHz and f2=915 MHz, because the attenuation at the frequencies f1, f2 is still sufficiently low as a result of the associated matching or tuning of the signal coupling elements 12, and hence of their attenuation curve 25. Thus, the length of the signal coupling elements 12 may be configured to be $\lambda/2$ for signals having a wavelength of $\lambda_{air}$=336 mm, corresponding to a center frequency of 892 MHz, that lies exactly in the center of the frequencies f1 and f2.

In a method step S1, a transfer characteristic of the antenna array 7 may be measured across all the coupling points 19 as a reference, for instance when the patient table 4 is unoccupied, i.e. without the patient 5. For this purpose, a defined transmitted signal may be given for one signal coupling element at a time of the signal coupling elements 12 in sequence, and a resultant received signal may be measured as the reference signal.

Alternatively, such a reference signal may be measured when the patient 5 is already arranged on the patient table 4, in which case, the patient may hold his breath, for example, in one or more different respiratory phases. A calibration of the detection apparatus for the given patient may be performed that provides for the respiratory movement or respiratory phases of the patient to be detected accurately and reliably.

In a method step S3, for the patient 5 placed on the patient table 4, the defined transmitted signal is given for one of the signal coupling elements 12, for instance onto the first signal coupling element 13, to detect the respiratory movement or respiratory phase of the patient. In a method step S4, a resultant received signal is then measured at another of the signal coupling elements 12, for instance at the second signal coupling element 14.

In a method step S5, the received signal is then analyzed to detect or determine the respiratory movement or the respiratory phase. In this step, given a continuous transmitted signal, a repeatedly reversing change in the received signal may be detected as the respiratory movement. The received signal or the change therein or deviation thereof from the transmitted signal may thus be analyzed to determine the respiratory movement or respiratory phase. The received signal, or the change therein or deviation thereof from the transmitted signal may also be compared with the previously acquired reference signal or deviation thereof from the transmitted signal.

As indicated schematically by a loop-shaped program path P1, the transmitted signal may be given for the antenna array 7 in a regularly repeated or continuous manner, and the respiratory movement or respiratory phase monitored by a corresponding regularly repeated or continuous analysis. Likewise, the signal coupling element of the signal coupling elements 12 that is acting as the transmitter may be interchanged for each cycle through the method steps S3 to S5 and program path P1. Thus, for instance, in a second cycle, for example after a specified timespan, the transmitted signal may be given for the second signal coupling element 14, that previously has served as the receiver. In this case, the received signal may then be measured or picked up at the third signal coupling element 15, for example, and so on. It is thereby possible to cycle through the signal coupling elements 12 in sequence to sample an entire surface area covered by the antenna array 7 for the purpose of detecting the respiratory movement. Detecting the respiratory phase incorrectly may hence be avoided reliably.

In summary, the examples described show how a U-shaped patch antenna may be used for detecting respiration.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A detection apparatus for detecting a respiratory movement of a patient, the detection apparatus comprising:
   at least three signal coupling elements that are U-shaped, the at least three signal coupling elements each comprising two side segments arranged in parallel to one another and a bottom segment connecting the two side segments, wherein the at least three signal coupling elements are arranged on a substrate such that the at least three signal coupling elements are interleaved without touching, so that between first and second side segments of a second signal coupling element of the at least three signal coupling elements, a second side segment of a first signal coupling element of the at least three signal coupling elements and a first side segment of a third signaling coupling element of the at least three signal coupling elements are arranged at least substantially parallel to the first and second side segments of the second signal coupling element, and a first side segment of the first signal coupling element and a second side segment of the third signal coupling element are arranged outside a region surrounded on three sides by the second signal coupling element;
   wherein the first signal coupling element is configured to transmit a first signal that is received by the second signal coupling element or the third signal coupling element that is interleaved with the first signal coupling element in a near-field region; and
   an electronic circuit connected to the at least three signal coupling elements, the electronic circuit configured to generate the first signal and detect a change in a second signal that is produced in the second signal coupling element or the third signal coupling element as a result of receiving the first signal transmitted by the first signal coupling element;
   wherein the change indicates the respiratory movement.

2. The detection apparatus of claim 1, wherein the at least three signal coupling elements are metallic.

3. The detection apparatus of claim 1, wherein the at least three signal coupling elements each have a length of between 16.1 cm and 17.6 cm.

4. The detection apparatus of claim 1, wherein the at least three signal coupling elements each have a length of 16.82 cm.

5. The detection apparatus of claim 1, wherein the at least three signal coupling elements are each made of a metallic layer of thickness 50 μm maximum.

6. The detection apparatus of claim 1, wherein the at least three signal coupling elements are each made of a metallic layer of thickness less than 25 μm.

7. The detection apparatus of claim 1, wherein the substrate is made of a plastic material and metalized on a rear face that faces away from the at least three signal coupling elements.

8. A method for detecting a respiratory movement of a patient, the method comprising:
   transmitting, by an electronic circuit, a first signal onto a first signal coupling element of a plurality of signal coupling elements, wherein the plurality of signal coupling elements comprise at least three signal coupling elements, the at least three signal coupling elements each comprising two side segments arranged in parallel to one another and a bottom segment connecting the two side segments, wherein the at least three signal coupling elements are arranged on a substrate such that the at least three signal coupling elements are interleaved without touching, so that between first and second side segments of a second signal coupling element of the at least three signal coupling elements, a second side segment of a first signal coupling element of the at least three signal coupling elements and a first side segment of a third signaling coupling element of the at least three signal coupling elements are arranged at least substantially parallel to the first and second side segments of the second signal coupling element, and a first side segment of the first signal coupling element and a second side segment of the third signal coupling element are arranged outside a region surrounded on three sides by the second signal coupling element, wherein only one of the plurality of signal coupling elements at a time functions as a transmitter, and one of the plurality of signal coupling elements that is coupled thereto functions as a receiver, wherein one of the plurality of signal coupling elements that is acting as a transmitter is interchanged as a function of a defined scheme according to a specified rhythm;
   measuring, by the electronic circuit, a second signal from the second signal coupling element or third signal coupling elements that is generated as a result of the first signal being transmitted by the first signal coupling element and being received by the second signal coupling element or the third signal coupling element that is interleaved with the first signal coupling element in a near-field region; and
   detecting the respiratory movement as a change in the second signal that occurs without a corresponding change in the first signal.

9. A medical device comprising:
   a detection apparatus for detecting a respiratory movement of a patient, the detection apparatus comprising:
      at least three signal coupling elements that are U-shaped and arranged on a substrate such that the at least three signal coupling elements are interleaved without touching, the at least three signal coupling elements each comprising two side segments arranged in parallel to one another and a bottom segment connecting the two side segments, wherein the at least three signal coupling elements are arranged on a substrate such that the at least three signal coupling elements are interleaved without touching, so that between first and second side segments of a second signal coupling element of the at least three signal coupling elements, a second side segment of a first signal coupling element of the at least three signal coupling elements and a first side segment of a third signaling coupling element of the at least three signal coupling elements are arranged at least substantially parallel to the first and second side segments of the second signal coupling element, and a first side segment of the first signal coupling element and a second side segment of the third signal coupling element are arranged outside a region surrounded on three sides by the second signal coupling element; and an electronic circuit connected to the at least three signal coupling elements, the electronic circuit configured to detect a change in a received signal produced in the second signal coupling element or the third signal coupling element of the signal coupling elements that are functioning as a receiver in a near-field region of the first signal coupling element; wherein the received signal is received as a result of a transmitted signal that is transmitted by the first signal coupling element of the signal coupling elements that is functioning as a transmitter; wherein the change indicates the respiratory movement; and a patient table including a reclining surface for the patient; wherein the at least three signal coupling elements of the detection apparatus are integrated in the patient table.

10. The medical device of claim 9, wherein the at least three signal coupling elements of the detection apparatus are integrated in the patient table in the reclining surface.

11. The medical device of claim 9, wherein the at least three signal coupling elements each have a length of between 16.1 cm and 17.6 cm.

12. The medical device of claim 9, wherein the at least three signal coupling elements each have a length of 16.82 cm.

13. The medical device of claim 9, wherein the at least three signal coupling elements are each made of a metallic layer of thickness 50 µm maximum.

14. The medical device of claim 9, wherein the at least three signal coupling elements are each made of a metallic layer of thickness less than 25 µm.

15. The medical device of claim 9, wherein the substrate is made of a plastic material and metalized on a rear face that faces away from the at least three signal coupling elements.

* * * * *